United States Patent [19]

Sardo

[11] Patent Number: 5,573,524
[45] Date of Patent: Nov. 12, 1996

[54] DISPOSABLE DIAPER WITH REFRESH ASSEMBLY

[76] Inventor: Nicholas Sardo, 25 Bayview Ave. East, Lindenhurst, N.Y. 11757

[21] Appl. No.: 498,608

[22] Filed: Jul. 6, 1995

[51] Int. Cl.$^6$ .................................... A61F 13/00
[52] U.S. Cl. ................. 604/385.1; 604/395; 604/358; 604/378
[58] Field of Search ................ 604/385.1, 358, 604/359, 378, 395, 400

[56] References Cited

U.S. PATENT DOCUMENTS

| | | | |
|---|---|---|---|
| 4,019,517 | 4/1977 | Glassman | 604/359 |
| 4,834,737 | 5/1989 | Khan | 604/395 |
| 4,964,857 | 10/1990 | Osborn | 604/395 |
| 4,968,311 | 11/1990 | Chickering et al. | 604/385.1 |
| 5,037,414 | 8/1991 | Booth | 604/385.1 |

Primary Examiner—Randall L. Green
Assistant Examiner—Bruce E. Snow
Attorney, Agent, or Firm—Kenneth P. Robinson

[57] ABSTRACT

A disposable diaper includes a refresh assembly configured to be activated while the diaper is worn, so as to provide an additional period of comfort until the diaper can be changed. The refresh assembly comprises an extendible panel having a length stored in a non-extended condition interior to a first diaper section. A pull line with line guide arrangement can be activated to extend the extendible panel between the interior of the diaper and the wearer. The extendible panel may include both a liquid impervious barrier, to isolate a wearer from a soiled portion of the diaper, and an absorbent layer to absorb moisture, thereby providing additional comfort to the wearer until the diaper can be changed.

8 Claims, 4 Drawing Sheets

5,573,524

DISPOSABLE DIAPER WITH REFRESH ASSEMBLY

This invention relates to disposable diapers, and more particularly to a new and improved disposable diaper which includes a diaper refresh assembly that is activated while being worn.

BACKGROUND OF THE INVENTION

The use of diapers of one form or another has been commonplace for many generations. More recently, the advent of disposable diapers, manufactured with modern materials, has lead to the quick decline in the use of reusable or washable diapers. Disposable diapers are convenient, sanitary and easy to change. Further, through the use of absorbent materials and elastic portions added around the leg wrapping regions, these diapers provide effective containment of liquid and solid waste.

However, as with older more conventional diapers, disposable diapers have not removed the need to somewhat quickly change the diaper after soiling. Failure to do so can result in wearer discomfort, rashes and the like. And although newer more advanced materials have been devised, regular and frequent diaper changes are still necessary.

There are times, however, when it is not practical or possible to change a soiled diaper. These situations include times when traveling in a car or when in public (e.g., shopping, etc.). In these situations, it would be a great help to be able to refresh the diaper currently in use in order to provide an additional period of wearer comfort, until a diaper change is possible.

Objects of the present invention are, therefore, to provide new and improved types of disposable diapers having one or more of the following features and capabilities:

—a refresh assembly useable to provide an additional period of comfort to the wearer;

—an easily activatable refresh assembly;

—a refresh assembly activatable while the diaper is worn; and

—a refresh assembly which may readily be incorporated into disposable diapers of various constructions during their manufacture.

SUMMARY OF THE INVENTION

In accordance with the invention, a disposable diaper includes a diaper refresh assembly. The basic diaper may be of the type which includes waist traversing first and second diaper sections extending between side fastening portions, a transversal section extending between the first and second diaper sections, an outer liquid impervious layer and at least one inner liquid absorbent layer. The diaper refresh assembly includes an extendible panel having two ends, with a first end fixed to the fist diaper section. The extendible panel has a length stored in a non-extended condition interior to the first diaper section and includes liquid absorbent material. At least one flexible pull line is attached to the second end of the extendible panel and extends along the transversal section to the second diaper section. The flexible pull line includes a grip portion stored adjacent to the second diaper section. A line guide structure extending interior to the transversal section is arranged to preliminarily constrain the flexible pull line and to enable activation of the pull line to extend the extendible panel. The extendible panel is extended between the liquid absorbent layer of the diaper and a wearer, while the disposable diaper is worn by the wearer.

For a better understanding of the invention, together with other and further objects, reference is made to the accompanying drawings, with the scope of the invention pointed out in the appended claims.

BRIEF DESCRIPTION OF THE DRAWINGS

In the drawings, like elements are assigned like reference numerals. The drawings are briefly described as follows.

DETAILED DESCRIPTION OF THE INVENTION

Figure 1:
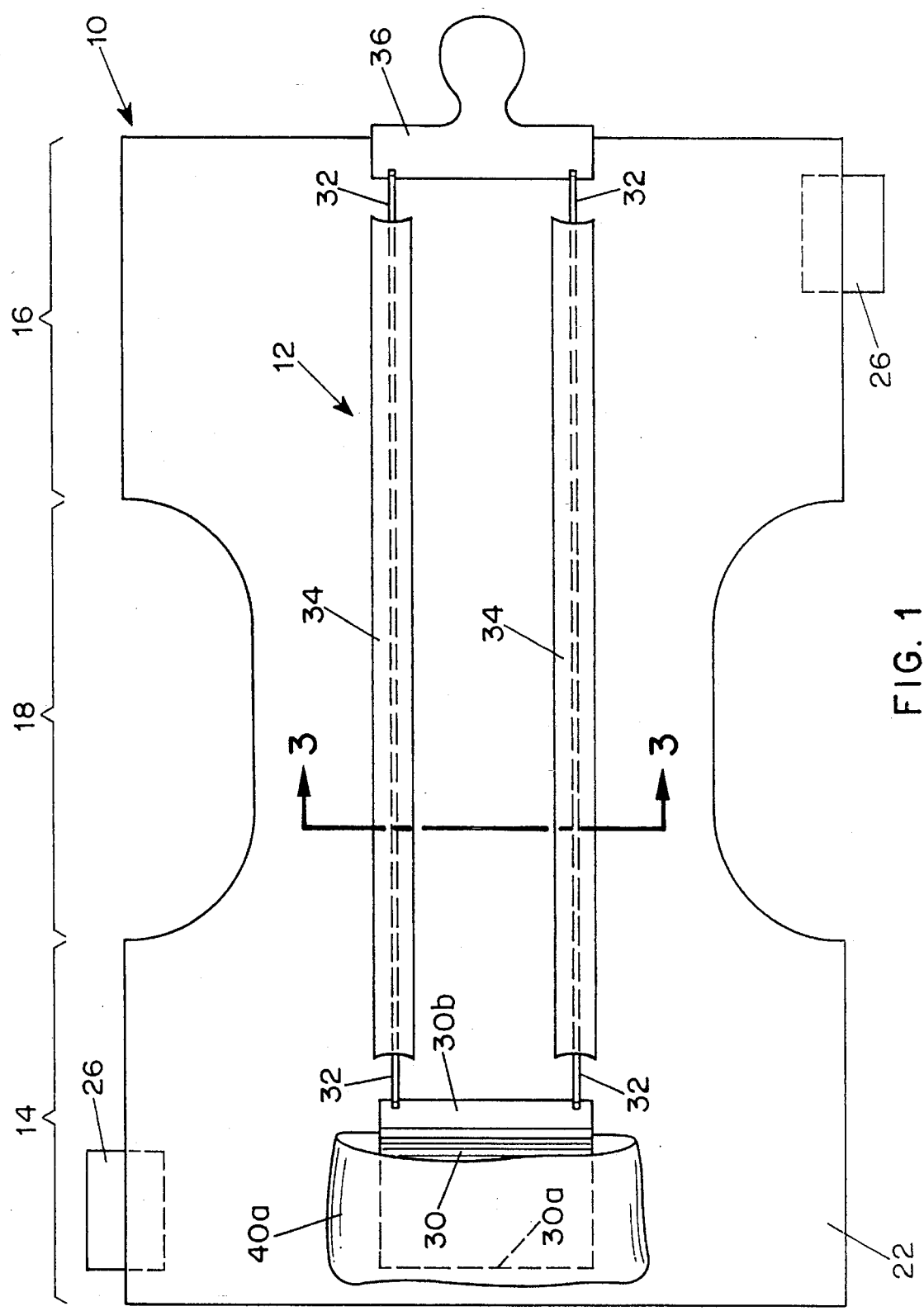
FIG. 1 provides a plan view of the interior of a disposable diaper having a diaper refresh assembly in accordance with the invention.

Referring now to FIG. 1, there is illustrated a disposable diaper 10 with a refresh assembly 12 configured in accordance with the present invention. As shown, the diaper includes a first diaper section 14, a second diaper section 16, and a transversal section 18. First section 14 and second section 16 are waist traversing diaper sections extending between fastening portions 26 when diaper 10 is being worn by a wearer. Fastening portions 26 may be provided as tape or other fastening arrangements, which are well known in the art. Also shown is the interior side of the diaper comprised of at least one liquid absorbent layer 22 which overlies an outer liquid impervious layer not visible in this view. The foregoing may be provided in known manner with a batting type of absorbent layer 22 serving as the inner layer positioned over an outer layer of thin flexible plastic material, for example.

Diaper refresh assembly 12 incorporated in diaper 10 comprises an extendible panel 30, which is shown in a non-extended condition, pull lines 32, line guide structure 34, and grip portion 36. Extendible panel 30 has a fixed first end 30a and an extendible second end 30b. First end 30a of extendible panel 30 is fixed to the interior of first section 14 of diaper 10. Pull lines 32 are attached to second end 30b of the extendible panel and extend along transversal section 18 to second diaper section 16, where they are attached to grip portion 36, which may have a variety of forms and shapes. Grip portion 36 is adjacent to second diaper section 16 and positioned so as to be reachable with diaper 10 being worn by the wearer. Also provided in FIG. 1 is line guide structure 34, included to preliminarily constrain pull lines 32 in position until refresh assembly 12 is activated, thereby extending extendible panel 30. A first pouch arrangement 40a may be provided to constrain extendible panel 30 while in the non-extended condition. Pouch 40a in the form of a thin plastic enclosure attached to diaper section 14 may optionally be included for initial storage of extendible panel 30. Panel 30 may be constructed of liquid absorbent material optionally backed by a thin sheet of liquid impervious plastic material.

Figure 2:
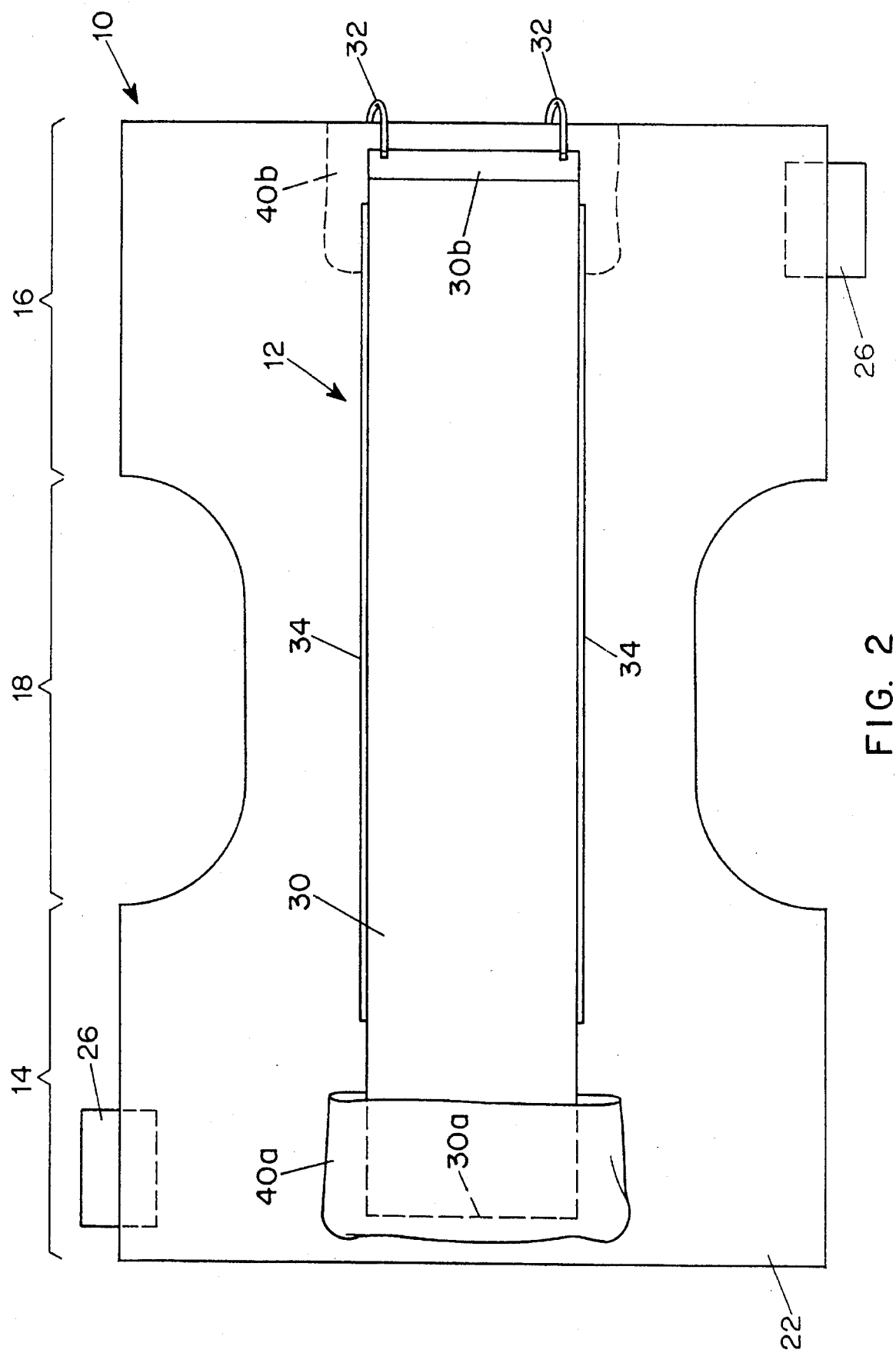
FIG. 2 shows the disposable diaper of FIG. 1 after the extendible panel has been extended.

Referring now to FIG. 2 there is illustrated a view of disposable diaper 10 after refresh assembly 12 has been activated. Extendible panel 30 is shown extended with second end 30b now positioned interior to second diaper section 16. In this position extendible panel 30 acts as a barrier and absorbent layer to refresh disposable diaper 10 by providing a fresh absorbent layer next to the wearer. Also shown in FIG. 2 is second pouch arrangement 40b, which may be provided to stow the pull lines and grip portion after extendible panel 30 has been extended. As illustrated second pouch arrangement 40b may be located on the exterior of diaper 10. Alternatively, pouch arrangement 40b can be provided between outer liquid impervious layer 20 and inner liquid absorbent layer 22.

Figure 3:
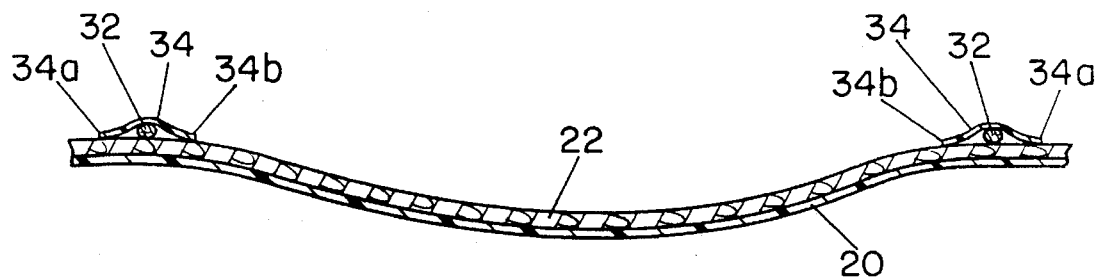
FIG. 3 is a sectional view of a portion of the diaper of FIG. 1.
Figure 3A:
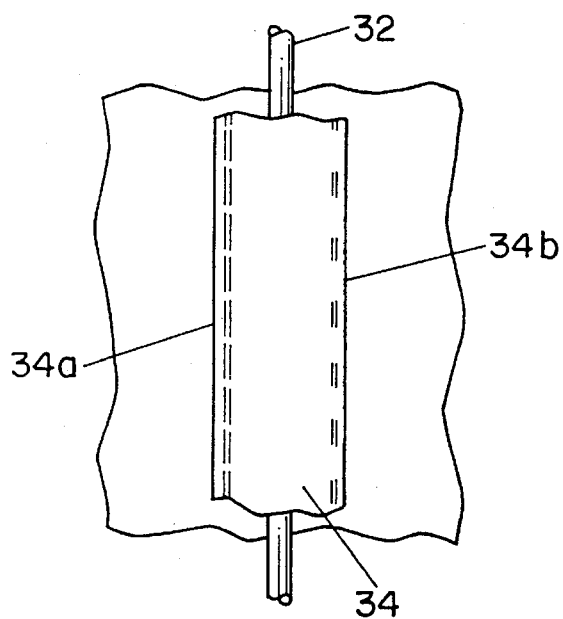
FIGS. 3A and 3B are top views of portions of two embodiments of the line guide structure of the FIG. 1 diaper.
Figure 4:
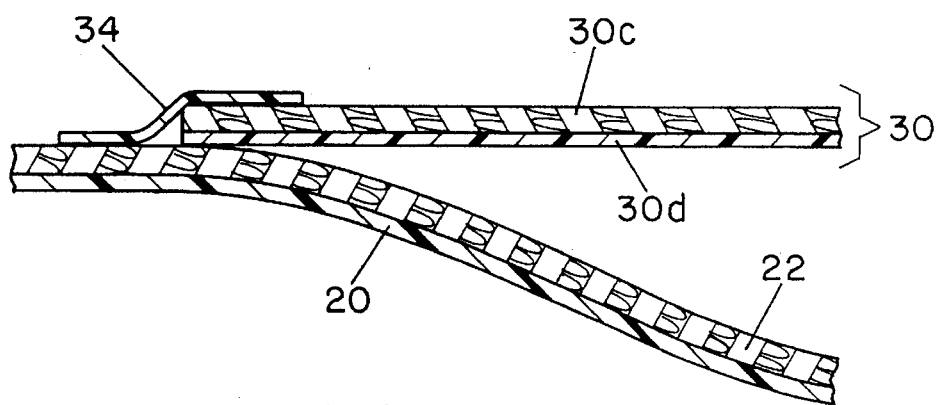
FIGS. 4, 4A and 4B are sectional views of portions of line guide structure embodiments after extension of the extendible panel.

With reference now to FIG. 3, there is shown a sectional, partial view of a portion of refresh assembly of diaper 10, prior to extension of panel 30. Provided is outer liquid impervious layer 20 covered by at least one inner liquid absorbent layer 22. The materials used to construct the layers of diaper 10 are well known by persons skilled in the art. Further provided in FIG. 3 are spaced pull lines 32 and a line guide structure comprised of thin sheet portions 34 covering pull lines 32. Thin sheet portions 34 are configured to preliminarily constrain the pull lines until diaper refresh assembly 12 is activated. Also indicated are inner edges 34b and outer edges 34a of thin sheet portions 34. The manner in which edges 34a and 34b are attached to the interior of diaper 10 vary with the particular embodiment of line guide structure utilized. FIG. 3A illustrates one example of how thin sheet portions 34 may be attached to the interior of diaper 10. With this embodiment, outer edge 34a is fixed to the interior of diaper 10, while inner edge 34b is frangibly tacked so as to give way on activation of pull lines 34. FIG. 4 illustrates the location of this sheet portion 34 of FIG. 3A, with respect to extendible panel 30, after the extension of extendible panel 30. Specific construction details can be selected by skilled persons. The outer edge 34a may, for example, connect to the adjacent edge of outer layer 20.

Figure 3B:
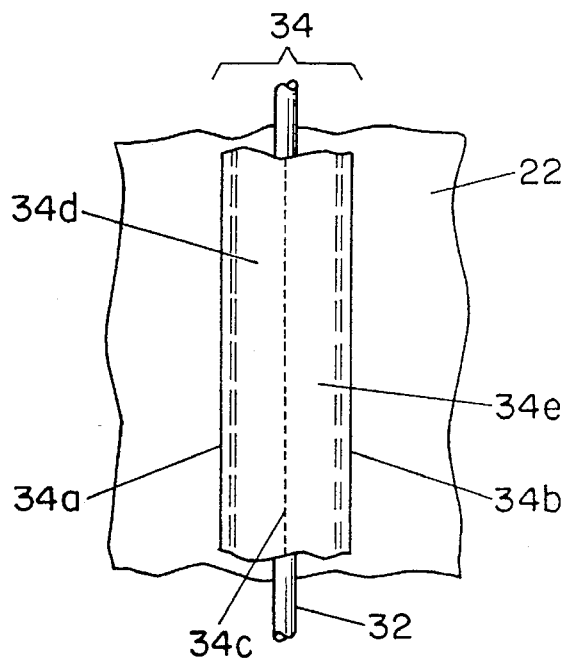
Figure 4A:
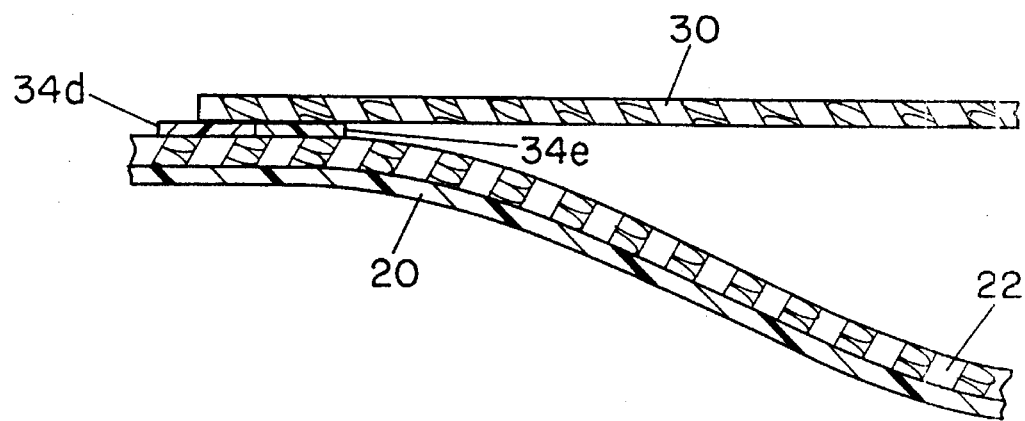
Figure 4B:
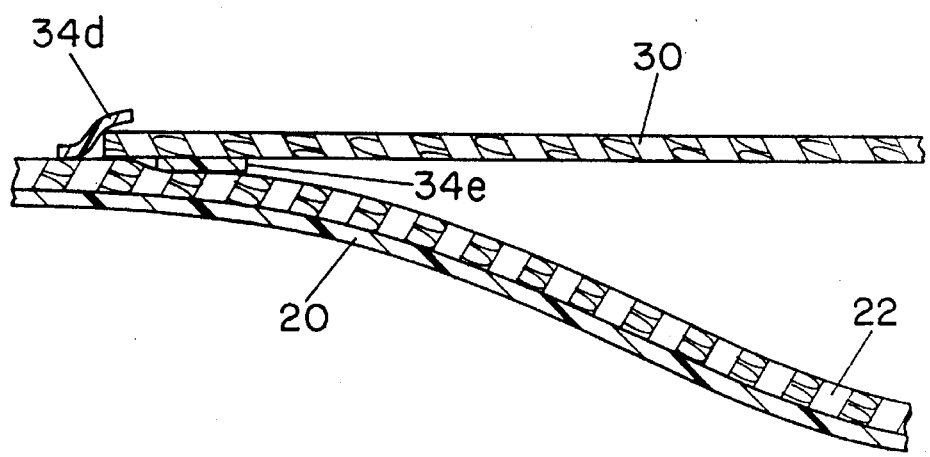

FIG. 3B shows another embodiment for configuring thin sheet portion 34. As shown in FIG. 3B, thin sheet portion 34 includes a perforation 34c that extends along its length. The perforation 34c effectively divides thin sheet portion 34 into two sections. Outer section 34d is associated with outer edge 34a, while inner section 34e is associated with inner edge 34b. It is important to note that with this embodiment both outer edge 34a and inner edge 34b are fixed to the interior of the diaper 10. On activation of pull line 32, extendible panel 30 tears thin sheet portion 34 along perforation 34c as extendible panel 30 is extended. FIGS. 4A and 4B provide partial sectional views of extendible panel 30 and thin sheet portion 34 after extendible panel 30 of FIG. 3B has been extended. FIG. 4A illustrates the respective locations of outer section 34d and inner section 34e of thin sheet portion 34 after extension for a configuration in which the width of the extendible panel is greater than the lateral spacing of thin sheet portions 34. In an alternate configuration, FIG. 4B shows the respective locations of outer section 34d and inner section 34e of thin sheet portions 34 of FIG. 3B after extension of extendible panel 30 when the width of the extendible panel is substantially equivalent to the lateral spacing of thin sheet portions 34.

Referring again to FIG. 4 there is further illustrated an extendible panel 30 comprised of a liquid impervious layer 30d, covered by a liquid absorbent layer 30c. This arrangement will provide a barrier to isolate a wearer from a soiled portion of absorbent layer 22, while presenting a refreshed moisture absorbing capability providing additional comfort to the wearer. It should be noted that individuals skilled in the art can provide a variety of configurations that may be used for construction of extendible panel 30.

Figure 5:
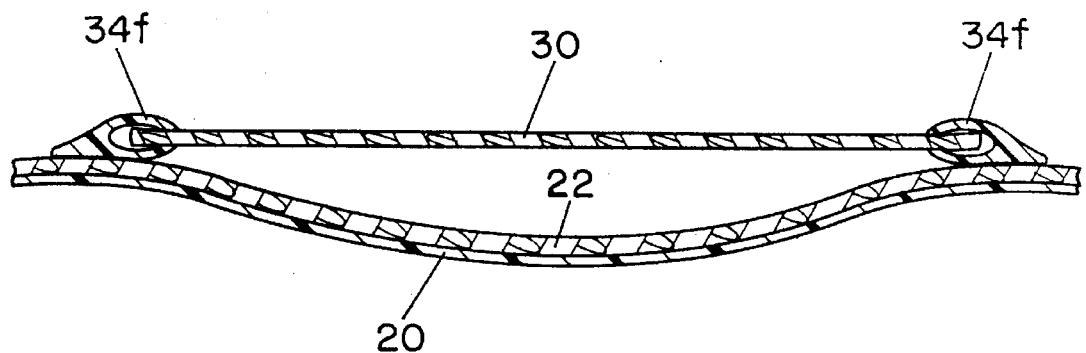
FIG. 5 illustrates an alternate embodiment of line guide structure of the FIG. 1 diaper after extension of the extendible panel.

Turning to FIG. 5 there is provided a partial sectional view of another embodiment of the line guide structure. Illustrated are two laterally spaced tracks 34f that are configured to slidably restrain the lateral edges of extendible panel 30. In a plan view such as FIG. 1, tracks 34f extend as indicated at 34. While the extendible panel 30 is in the non-extended condition, pull lines 32 are preliminarily constrained within tracks 34f. When pull lines 32 are activated, extendible panel 30 is extended, being slidably guided through tracks 34f. The FIG. 5 embodiment provides the additional advantage that the extended panel 30 is restrained at its edges within the tracks 34f. Tracks 34f may be formed of flexible plastic or other suitable material with a longitudinal cut providing access to a small internal cavity and a flat tab facilitating attachment to the diaper, as illustrated in this embodiment. Pull lines 32 are thus enabled to pull the edges of panel 30 through the tracks 34f.

While there have been described the currently preferred embodiments of the invention, those skilled in the art will recognize that other and further modifications may be made without departing from the invention and it is intended to claim all modifications and variations as fall within the scope of the invention.

What is claimed is:

1. A disposable diaper of the type including waist traversing first and second diaper sections extending between side fastening portions and a transversal section extending between said first and second diaper sections, said disposable diaper having an outer liquid impervious layer and at least one inner liquid absorbent layer and additionally including a diaper refresh assembly, comprising:

an extendible panel having two ends, with a first end fixed to said first diaper section and a length stored in a non-extended condition interior to said first diaper section, said extendible panel including liquid absorbent material;

at least one flexible pull line attached to said second end of said extendible panel and extending along said transversal section to said second diaper section, said at least one flexible pull line including a grip portion stored adjacent to said second diaper section; and a line guide structure extending interior to said transversal section and arranged to preliminarily constrain said at least one flexible pull line and to enable activation of said pull line to extend said extendible panel between said liquid absorbent layer of said diaper and a wearer, while said disposable diaper is worn by said wearer.

2. A disposable diaper including a diaper refresh assembly as in claim 1, wherein said at least one flexible pull line comprises two laterally spaced pull lines each extending from said second end of said extendible panel to said second diaper section.

3. A disposable diaper including a diaper refresh assembly as in claim 2, wherein said line guide structure comprises thin sheet portions covering said pull lines to preliminarily constrain said pull lines, said thin sheet portions frangibly attached to said disposable diaper so as to give way on activation of said pull lines to extend said extendible panel.

4. A disposable diaper including a diaper refresh assembly as in claim 2, wherein said line guide structure comprises thin sheet portions fixed to said disposable diaper and covering said pull lines to preliminarily constrain said pull lines, said thin sheet portions being perforated, so as to tear on activation of said pull lines to extend said extendible panel.

5. A disposable diaper including a diaper refresh assembly as in claim 1, wherein said line guide structure comprises two laterally spaced tracks configured to slidably restrain the lateral edges of said extendible panel when extended by activation of said at least one pull line.

6. A disposable diaper including a diaper refresh assembly as in claim 1, wherein said extendible panel consists of a layer of liquid absorbent material.

7. A disposable diaper including a diaper refresh assembly as in claim 1, wherein said extendible panel comprises a layer of liquid impervious material covered by a layer of liquid absorbent material, said extendible panel arranged to extend closes to said wearer.

8. A disposable diaper including a diaper refresh assembly as in claim 1, further comprising a pouch arrangement to support said extendible panel in said non-extended condition.

\* \* \* \* \*